United States Patent
Hopkins et al.

(10) Patent No.: US 9,763,797 B2
(45) Date of Patent: Sep. 19, 2017

(54) SHOULDER PROSTHESIS AND COMPONENTS THEREOF

(71) Applicant: ZIMMER GMBH, Winterthur (CH)

(72) Inventors: Andrew Hopkins, Winterthur (CH); Philippe Hardy, Paris (FR)

(73) Assignee: ZIMMER GMBH (CH)

( * ) Notice: Subject to any disclaimer, the term of this patent is extended or adjusted under 35 U.S.C. 154(b) by 0 days.

(21) Appl. No.: 14/439,605

(22) PCT Filed: Dec. 19, 2013

(86) PCT No.: PCT/EP2013/077419
§ 371 (c)(1),
(2) Date: Apr. 29, 2015

(87) PCT Pub. No.: WO2014/102141
PCT Pub. Date: Jul. 3, 2014

(65) Prior Publication Data
US 2015/0289985 A1 Oct. 15, 2015

(30) Foreign Application Priority Data
Dec. 27, 2012 (EP) .................... 12199430

(51) Int. Cl.
*A61F 2/40* (2006.01)
*A61F 2/30* (2006.01)

(52) U.S. Cl.
CPC .............. *A61F 2/40* (2013.01); *A61F 2/4014* (2013.01); *A61F 2/4081* (2013.01);
(Continued)

(58) Field of Classification Search
CPC ........ A61F 2/40; A61F 2/4014; A61F 2/4081; A61F 2/3868; A61F 2/3872; A61F 2002/4085
See application file for complete search history.

(56) References Cited

U.S. PATENT DOCUMENTS

| 4,003,095 A | * | 1/1977 | Gristina | .................... A61F 2/40 623/19.12 |
| 5,336,267 A | * | 8/1994 | Kubein-Meesenburg | ............. A61F 2/32 623/23.39 |

(Continued)

FOREIGN PATENT DOCUMENTS

| EP | 0850609 A1 | 7/1998 |
| EP | 1393697 B1 | 2/2006 |

(Continued)

OTHER PUBLICATIONS

"International Application Serial No. PCT/EP2013/077419, International Preliminary Report on Patentability mailed Jun. 30, 2015", 9 pgs.

(Continued)

*Primary Examiner* — Brian Dukert
(74) *Attorney, Agent, or Firm* — Schwegman Lundberg & Woessner, P.A.

(57) ABSTRACT

The present disclosure relates to a shoulder prosthesis comprising a glenoidal component having a glenoidal articulation surface and a humeral component having a humeral articulation surface, and a separate mobile glenohumeral bearing component comprising a glenoidal bearing surface and a humeral bearing surface arranged on opposite sides of the glenohumeral bearing component. The glenoidal bearing surface contacts in an implanted state the glenoidal articulation surface and/or the humeral bearing surface contacts in an implanted state the humeral articulation surface. At least one of the glenoidal and humeral bearing surfaces is concave. The glenohumeral bearing component is disposed in an implanted state between the glenoidal component and the humeral component. Both the glenoidal and humeral articulation surfaces are convex.

16 Claims, 5 Drawing Sheets

(52) U.S. Cl.
CPC . *A61F 2002/302* (2013.01); *A61F 2002/4018* (2013.01); *A61F 2002/4085* (2013.01)

(56) References Cited

U.S. PATENT DOCUMENTS

| | | | |
|---|---|---|---|
| 5,593,445 | A | 1/1997 | Waits |
| 5,723,018 | A | 3/1998 | Cyprien et al. |
| 7,799,077 | B2 | 9/2010 | Lang et al. |
| 9,408,652 | B2 | 8/2016 | Hassler et al. |
| 2006/0009852 | A1* | 1/2006 | Winslow ............ A61B 17/1684 623/19.14 |
| 2009/0112328 | A1 | 4/2009 | Tornier et al. |
| 2009/0287309 | A1 | 11/2009 | Walch et al. |
| 2011/0098822 | A1 | 4/2011 | Walch et al. |
| 2013/0053969 | A1 | 2/2013 | Linares et al. |
| 2017/0105843 | A1 | 4/2017 | Britton et al. |

FOREIGN PATENT DOCUMENTS

| | | |
|---|---|---|
| EP | 1649836 A2 | 4/2006 |
| EP | 1598034 B1 | 3/2011 |
| EP | 2382930 A1 | 11/2011 |
| EP | 2749255 A1 | 7/2014 |
| WO | WO-9410941 | 5/1994 |
| WO | WO-2007057054 A1 | 5/2007 |
| WO | WO-2014102141 A1 | 7/2014 |
| WO | WO-2017066504 A1 | 4/2017 |

OTHER PUBLICATIONS

"International Application Serial No. PCT/EP2013/077419, International Search Report mailed Jan. 30, 2014", 5 pgs.

"International Application Serial No. PCT/US2016/056935, International Search Report dated Jan. 18, 2017", 6 pgs.

"International Application Serial No. PCT/US2016/056935, Written Opinion dated Jan. 18, 2017", 7 pgs.

* cited by examiner

SHOULDER PROSTHESIS AND COMPONENTS THEREOF

PRIORITY APPLICATIONS

This application is a U.S. National Stage Filing under 35 U.S.C. 371 from International Application No. PCT/EP2013/077419, filed on 19 Dec. 2013, and published as WO/2014/102141 on 3 Jul. 2014, which application claims the benefit under 35 U.S.C. 119 to EP Application No. 12199430.5, filed on 27 Dec. 2012; which applications and publication are incorporated herein by reference in their entirety.

The present disclosures relates to a shoulder prosthesis to be used in shoulder arthroplasty.

Shoulder pathology often involves disruption of the glenohumeral joint and/or an impairment of its functional components. A suitable treatment can involve a prosthetic replacement of the affected components of the natural joint. A partial reconstruction of the glenohumeral joint comprises the replacement of the natural articulation surface of the glenoidal component or the humeral component of the shoulder. In a complete reconstruction of the glenohumeral joint—also referred to as total shoulder arthroplasty (TSA)—both of the natural components mentioned above are replaced by prosthetic implants.

Documents EP 0 850 609 A1, US 2009/0112328 A1, U.S. Pat. No. 7,799,077 B2 and U.S. Pat. No. 5,593,445 A disclose exemplary shoulder joint prostheses with kinematics mimicking in principle the kinematics of a natural shoulder joint, i.e. the humeral component of the prostheses is provided with a convex articulation surface. Document EP 1 649 836 A2 discloses a prosthesis with an inverse kinematics. A further exemplary shoulder joint prosthesis is disclosed by WO 94/10941 A1.

Here, a novel concept of a shoulder prosthesis is suggested that has improved kinematics and that can be reliably fixed to the bone components involved.

The shoulder prosthesis according to claim 1 is provided with a glenoidal component having a glenoidal articulation surface and a humeral component having a humeral articulation surface. In other words, it is possible to provide a shoulder prosthesis comprising only a glenoidal component or a humeral component. Further, a separate mobile glenohumeral bearing component comprising a glenoidal bearing surface and a humeral bearing surface arranged on opposite sides of the glenohumeral bearing component is provided. The glenoidal bearing surface contacts in an implanted state the glenoidal articulation surface. Alternatively or additionally, the humeral bearing surface contacts in an implanted state the humeral articulation surface. At least one of the glenoidal and humeral bearing surfaces is concave.

Such a design has the advantages of a mobile bearing that acts as interpositional spacer while being very compact and having advantageous kinematic properties. The concave shape of at least one of the bearing surfaces brings the articulation close to the center of the prosthesis leading to an articulation kinematics that resembles closely the natural articulation. Further, a reduction of the stress and strain exerted on the components of the prostheses and adjacent portions the humerus and/or the scapula can be achieved.

"Mobile" in the context of the present disclosure should be understood as not being mounted to any bone or any other prosthetic component. Hence, the glenohumeral bearing component is merely in articulation contact with the glenoidal component and/or humeral component and is not provided with bone attachment means that secure the glenohumeral bearing component to one or both of said components. The glenohumeral bearing component is thus allowed to move—constrained only by the shape of the interacting surfaces—in reaction to a relative displacement and/or relative rotation of these components. The glenohumeral bearing component can therefore assume automatically an optimal position that reduces contact stresses acting between the functional elements involved.

The glenoidal articulation surface is convex. Hence, the glenoidal articulation surface of the glenoidal component is inverted compared to the natural osseous anatomy shifting the focus of the articulation towards the humeral head.

In yet another embodiment of the shoulder prosthesis, the glenoidal and humeral bearing surfaces have different curvatures and/or sizes to obtain the desired articulation kinematics of the prosthesis. In particular, the glenoidal bearing surface is smaller than the glenoidal articulation surface and/or the humeral bearing surface is smaller than the humeral articulation surface. However, in one embodiment the curvatures and/or the sizes of said surfaces are similar or identical. It is thus possible to choose said parameters as needed to realize the desired articulation kinematics.

According to another embodiment of the shoulder prosthesis according to the present disclosure, the glenohumeral bearing component comprises a central recess in the glenoidal bearing surface and/or the humeral bearing surface. Alternatively, a central opening extending from the glenoidal bearing surface to the humeral bearing surface may be provided. In other words, the glenohumeral bearing component may be provided with a recess and/or a hole in or close to the center of the bearing component in order to reduce the weight of the bearing component without comprising its functionality.

The shoulder prosthesis comprises both the glenoidal component and the humeral component, wherein the glenohumeral bearing component is disposed in an implanted state between the glenoidal component and the humeral component. Thus, the glenoidal component and the humeral component are not in direct contact and the glenohumeral bearing component acts as interpositional-spacer between the prosthetic articulation surfaces of said components. Both the glenoidal and humeral articulation surfaces are convex to concentrate the kinematic center of the prosthesis on the glenohumeral bearing component. In such an embodiment, both the bearing surfaces of the glenohumeral bearing component are concave, so that the spatial separation of the articulation surfaces—natural or prosthetic—is rather small in an implanted state of the prosthesis. This concept is in particular suited in cases where a total shoulder arthroplasty is indicated.

In another embodiment of the shoulder prosthesis, the glenoidal component comprises a glenoidal bone interface provided to be attached to the scapula of a patient and/or the humeral component comprises a humeral bone interface provided to be attached to a humerus of the patient, wherein the glenoidal bone interface or the humeral bone interface of the respective implant component is concave. In particular, both the glenoidal and humeral bone interfaces of the respective implant component are concave. Providing the glenoidal bone interface and/or the humeral bone interface with a concave design reduces tensile stress acting between the bone interface and the bone, especially when eccentric loads are applied. A concave geometry realigns the loads towards the center thereby reducing the occurrence of tensile stress that are particularly detrimental to the fixation reliability at the margin of the respective prosthetic component.

In other words, the load distribution acting on the subchondral bone underlying the prosthetic component is improved by providing said component with a concave bone interface. Further, the surgical impact associated with implanting a shoulder prosthesis with a concave glenoidal bone interface and/or a concave humeral bone interface is reduced since less bone material has to be resected. Moreover, as bone material is preserved the convex bone surface adapted to receive such a concave bone interface can—if necessary—be converted by resection relatively easily into a planar or concave surface in case the respective prosthetic component has to be replaced. It should be noted that the advantageous effects associated with a concave bone interface can in principle also be realised in shoulder prosthesis which are not provided with a mobile bearing component and/or which are provided with a bearing component without at least one concave bearing surface.

The glenoidal bone interface may be disposed on a glenoidal base element that couples with an articulation element of the glenoidal component carrying the glenoidal articulation surface via a first coupling means and/or the humeral bone interface may be disposed on a humeral base element that couples with an articulation element of the prosthetic humeral component carrying the humeral articulation surface via a second coupling means. Said first and/or second coupling means may comprise at least one screw, a taper and/or snap means. In other words, the glenoidal component and/or the humeral component may comprise at least two separate elements provided with different functionalities. For example, first the corresponding base element is fixed to the bone and the articulation element is attached to the base element after it has been made sure that the base element is reliably fixed to the bone. Such an approach may facilitate the implantation of the shoulder prosthesis.

According to an embodiment of the shoulder prosthesis, the glenohumeral bearing component is made of ceramic and/or polyethylene. The glenoidal component—if applicable the glenoidal articulation element and/or the glenoidal base element—and/or the humeral component—if applicable the humeral articulation element and/or the humeral base element—may be made of metal, metal alloy, ceramic and/or polyethylene.

To be able to mimic the natural articulation of a shoulder joint and/or to provide the patient with a shoulder prosthesis adapted to his specific needs, the respective curvatures of the articulation surfaces and of the bearing surfaces have to be adjusted accordingly. However, it is not imperative that the articulation surfaces have identical curvatures or that the bearing surfaces have identical curvatures. It is also not imperative to provide the bearing surfaces with the same curvature as the corresponding articulation surfaces. In particular, the curvature of the glenoidal articulation surface and the curvature of the humeral articulation surface may be different from each other and different from that of the corresponding bearing surface. Specifically, the curvature of a concave surface may be smaller than that of the corresponding convex surface with which it is in contact.

Apart from the curvature of the cooperating surfaces, the thickness and the diameter of the glenohumeral component play an important role in determining the kinematics of the shoulder prosthesis. Hence, these parameters may also be chosen freely to achieve the desired kinematics.

Another important aspect influencing the kinematics of the shoulder prosthesis is the friction between the components of the shoulder prosthesis during articulation. In an embodiment of the shoulder prosthesis according to the present disclosure, the glenoidal articulation surface, the humeral articulation surface, the glenoidal bearing surface and the humeral bearing surface are designed such and/or the materials of said components are chosen such that a first coefficient of friction between the glenoidal articulation surface and the glenodial bearing surface and a second coefficient or friction between the humeral articulation surface and humeral bearing surface are essentially equivalent. However, different coefficients of friction may be envisaged to create specific kinematic situations in order to meet the individual needs of a given patient. Different coefficients of friction may focus the kinematics and/or the associated loads on the humeral side or the glenoidal side of the shoulder prosthesis.

Further, a prosthetic glenoidal component of a shoulder prosthesis is suggested that reduces tensile loads acting between said component and the bone to which it is fixed.

Said prosthetic glenoidal component comprises a glenoidal articulation surface adapted to cooperate directly or indirectly via a glenohumeral bearing component with a natural or with a prosthetic humeral articulation surface. Said prosthetic glenoidal component further comprises a glenoidal bone interface provided to be attached to the scapula of a patient, wherein the glenoidal bone interface is concave. The advantages associated with a concave bone interface have been described in detail above in connection with a shoulder prosthesis according to the present disclosure. These considerations apply analogously to the prosthetic glenoidal component according to the present disclosure.

According to an embodiment of the prosthetic glenoidal component, the glenoidal articulation surface is convex.

Further, a glenohumeral bearing component is suggested that is adapted to be used in a shoulder prosthesis according to any of the embodiments described above.

In an embodiment of the glenohumeral bearing component, the glenohumeral bearing component comprises a glenoidal bearing surface and a humeral bearing surface arranged on opposite sides of the glenohumeral bearing component. One of the glenoidal bearing and the humeral bearing surfaces is concave and the other of the glenoidal bearing and the humeral bearing surfaces is one of planar, convex or concave.

A method for implanting a shoulder prosthesis is suggested, comprising the steps of providing a prosthetic glenoidal component comprising a glenoidal articulation surface and/or providing a prosthetic humeral component comprising a humeral articulation surface, resecting a glenoidal portion of a patient's scapula and attaching the glenoidal component to the resected glenoidal portion and/or resecting a proximal end of a patient's humerus and attaching the humeral component to the resected proximal end portion, and inserting a glenohumeral bearing component comprising a glenoidal bearing surface and a humeral bearing surface, wherein the glenoidal bearing surface contacts in an implanted state the glenoidal articulation surface and/or wherein the humeral bearing surface contacts in an implanted state the humeral articulation surface. At least one of the glenoidal and humeral bearing surfaces is concave.

According to an embodiment of the method, the step of resecting the glenoidal portion of a patient's scapula comprises the step of preparing a convex bone portion adapted to match a correspondingly shaped—in particular concave—bone interface of the glenoidal component.

In another embodiment of the method, the step of providing a glenoidal component comprises providing a glenoidal component comprising a convex glenoidal articulation surface.

In yet another embodiment of the method, the step of attaching the glenoidal component to the resected glenoidal portion comprises placing the glenoidal component on the convex bone portion and fixing it to the scapula using at least one of a screw, bone cement and a press fit means.

A further method of implanting a shoulder prosthesis comprises the steps of providing a prosthetic glenoidal component comprising a glenoidal articulation surface and a glenoidal bone interface provided to be attached to a scapula of a patient, resecting a glenoidal portion of a patient's scapula to form a convex bone portion adapted to match the correspondingly shaped—in particular concave—glenoidal bone interface and fixing the glenoidal component to the resected glenoidal portion.

The different embodiments of the shoulder prosthesis, the prosthetic glenoidal component, the glenohumeral bearing component and the methods of implanting a shoulder prosthesis described above in accordance with the scope of the independent claims and the features realized there can naturally be combined with one another.

Further embodiments of the disclosure are also recited in the dependent claims, the description and the drawings.

Further areas of applicability of the present disclosure will become apparent from the detailed description provided hereinafter. It should be understood that the detailed description and the specific examples are intended for purpose of illustration only and are not intended to limit the scope of the invention in any way. The figures are simplified in schematic. Details not necessary for the understanding of the invention are omitted.

The present disclosure will be explained in more detail and become fully understood from the detailed description and the accompanying drawings, wherein.

Figure 1:
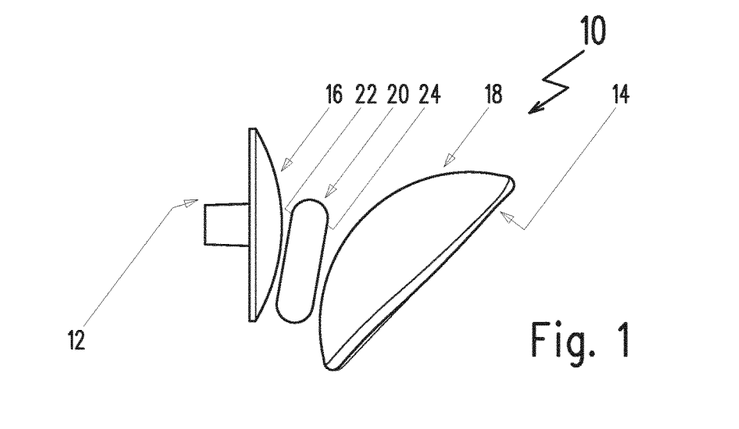
FIGS. 1 and 2 depict an embodiment of the shoulder prosthesis in accordance with the present disclosure in different perspective views.

FIG. 1 shows a shoulder prosthesis 10 comprising a glenoidal component 12 attached in an implanted state to a scapula of a patient and a humeral component 14 attached in an implanted state to a humeral head of the humerus of a patient. Glenoidal component 12 comprises—contrary to the natural anatomy—a convex glenoidal articulation surface 16. Humeral component 14 is provided with a humeral articulation surface 18.

In an implanted state, surfaces 16, 18 are not in direct contact with each other but are separated by glenohumeral bearing component 20. Glenohumeral bearing component 20 therefore acts as a spacer disposed between components 12, 14. Glenohumeral bearing component 20 comprises a glenoidal bearing surface 22 that is in an implanted state of prosthesis 10 in contact with glenoidal articulation surface 16. On the opposite side, glenohumeral bearing component 20 is provided with humeral bearing surface 24 that is in an implanted state of prosthesis 10 in contact with humeral articulation surface 18.

Glenohumeral bearing component 20 is not attached to neither of components 12, 14. It can therefore move freely relative to surfaces 16, 18. The movement of glenohumeral bearing component 20 relative to components 12, 14 is in essence governed by the geometry and properties of surfaces 16, 18, 22, 24 and the loads applied to the prosthesis during articulation of the shoulder. In other words, glenohumeral bearing component 20 is a separate, mobile component and shoulder prosthesis 10 can be described as a mobile bearing shoulder system particularly suitable for total shoulder arthroplasty intended for patients who have intact and functional rotor cuff musculature. However, it should be understood, that the principle of the shoulder prosthesis according to the present disclosure can also be applied to prostheses used in partial shoulder arthroplasty in which e.g. the natural humeral head is preserved.

Figure 2:
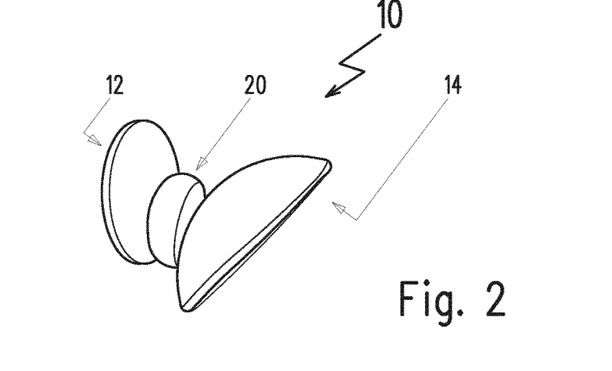

FIG. 2 shows shoulder prosthesis 10 in an perspective view to display the lens-like design of glenohumeral bearing component 20. In this example, the glenohumeral bearing component 20 has the shape of a concave-concave lens. However, it should be appreciated that convex-concave or concave-convex designs are also conceivable.

Figure 3:
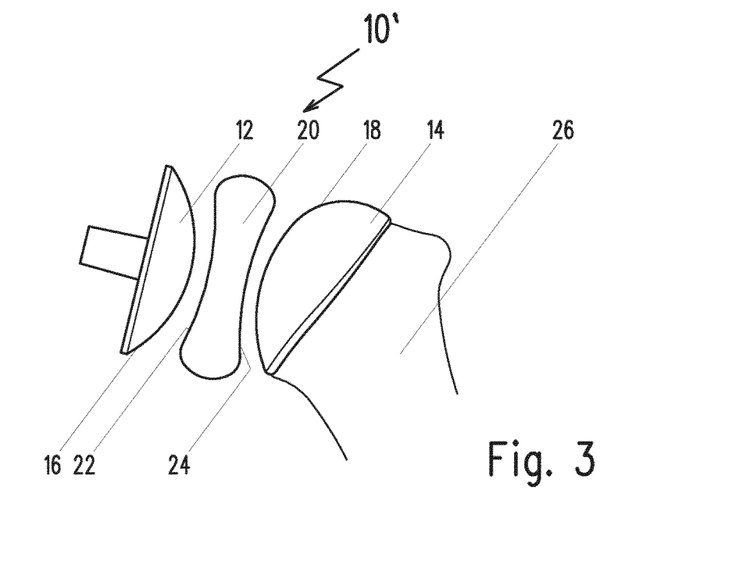
FIG. 3 shows schematically a similar embodiment of the shoulder prosthesis in accordance with the present disclosure.

FIG. 3 shows schematically a shoulder prosthesis 10' which is functionally similar to shoulder prosthesis 10. Humeral component 14 of shoulder prosthesis 10' is fixed to the proximal end of humerus 26 replacing—at least partially—its head. The natural articulation surface of humerus 26 has therefore been substituted by prosthetic articulation surface 18 of humeral component 14.

It can be seen from FIG. 3 that both bearing surfaces 22, 24 of glenohumeral bearing component 20 are concave and that no attachment means are provided to secure or fix component 20 to one of or both components 12, 14. A movement of glenohumeral bearing component 20 relative to components 12, 14 during articulation of the shoulder is constrained by the geometry of surfaces 16, 18, 22, 24, the loads applied and the friction between surfaces 16, 22 on the one hand and the friction between surfaces 18, 24 on the other hand. Due to the concave design of surfaces 22, 24, the kinematics of shoulder prosthesis 10'- and similarly the kinematics of prosthesis 10—concentrates close to the center of glenohumeral bearing component 20. In contrast, if surfaces 22, 24 would be both convex, the motion of glenoidal component 12 relative to glenohumeral component 20 on one the hand and the motion of humeral component 14 relative to glenohumeral bearing component 20 one the other hand would be spatially separated substantially leading to an unnatural overall articulation kinematics. Hence, shoulder prosthesis 10' combines the advantages of a mobile bearing system with a compact design without compromising a natural articulation.

In other words, the mobile bearing concept of the present disclosure comprises a glenohumeral bearing component 20 that is compact—in most cases smaller than components 12, 14—and that is free to articulate and to move between components 12, 14. The geometry of surfaces 16, 18, 22, 24 and the loads applied during articulation create forces that automatically shift glenohumeral bearing component 20 in the optimal position which leads to a reduction of contact stresses.

Moreover, the concave design of surfaces 22, 24 allows providing a mobile bearing prosthesis with a minimized distance between components 12, 14 which in turn reduces the surgical impact of the implantation of a shoulder prosthesis according to the present disclosure.

Figure 4:
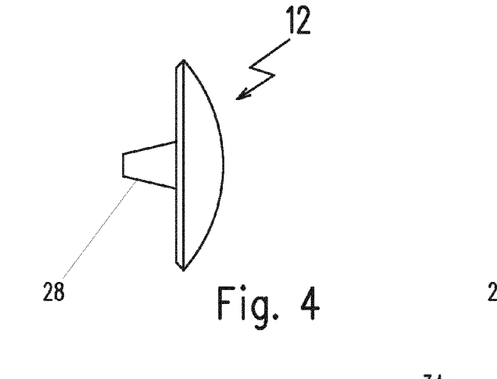
FIGS. 4 and 5 show schematically an embodiment of the prosthetic glenoidal component in accordance with the present disclosure.

FIG. 4 shows glenoidal component 12 of prosthesis 10' in a sideview. Glenoidal component 12 can be attached to the scapula of a patient via tapered peg 28. In principle, all known concepts of attaching a prosthesis to a bone can be contemplated when choosing a suitable approach to fix component 12 to the scapula. The same applies to means and methods for fixing humeral component 14 to humerus 26.

Figure 5:
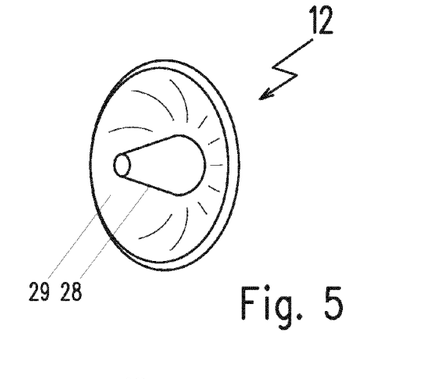

FIG. 5 shows schematically glenoidal component 12 from the bone interface side to visualize the geometry of a bone interface surface 29 of glenoidal component 12. It is not flat but has a concave shape from which peg 28 extends.

Figure 6:
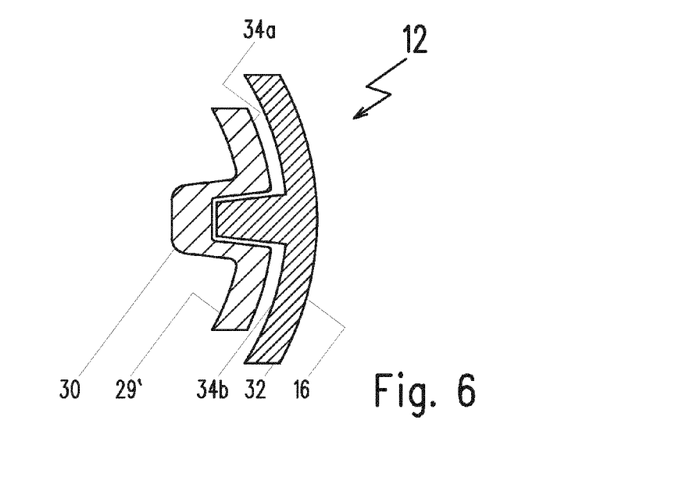
FIG. 6 shows an embodiment of the prosthetic glenoidal component comprising a base element and an articulation element.

As depicted in FIG. 6, instead of a direct fixation of glenoidal component 12 to the scapula, it may be envisaged to provide a glenoidal component 12' with a base element 30 comprising a concave bone interface surface 29'. Base element 30 receives an articulation element 32 comprising glenoidal articulation surface 16. Glenoidal component 12' therefore comprises two separate elements 30, 32 with different functionalities. Base element 30 and articulation element 32 of glenoidal component 12' comprise convex and concave contacting surfaces 34a, 34b, respectively, which are in contact in an assembled state of glenoidal component 12'.

Exemplarily, first base element 30 is attached to the bone during implantation of component 12'. Then, articulation element 32 is attached to base element 30 in a following step. Thus, base element 30 serves as an anchor that allows to fix articulation element 32 to the bone. It should be understood that humeral component 14 may be designed analogously.

Figure 7A:
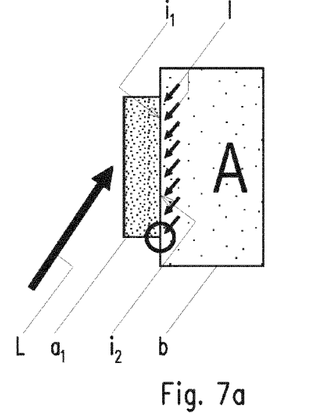
FIGS. 7*a* to 7*c* show load distributions resulting from different bone interface geometries.
Figure 7B:
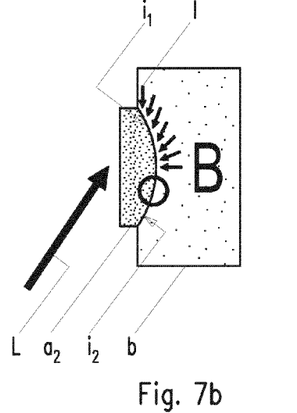
Figure 7C:
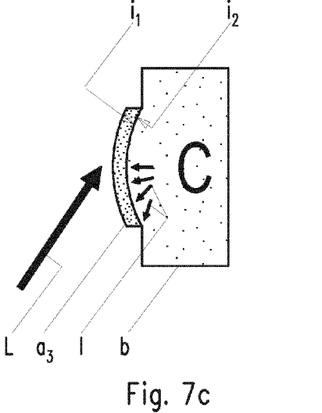

FIGS. 7a to 7c show the effect of the geometry of the bone interface surface on the stress and strain regime during articulation in a generalized form.

In all shown cases the load acting on a prosthetic component or implant $a_1$, $a_2$, $a_3$ attached to a bone b is depicted by arrow L. The resultant stress produced in bone b is indicated by small arrows l.

Figure 8A:
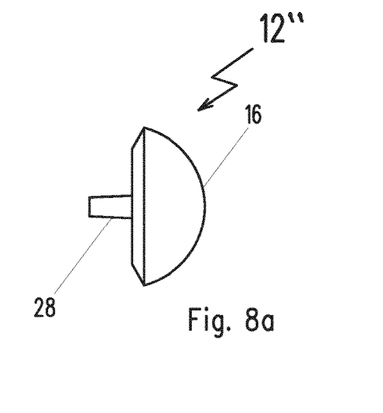
FIGS. 8*a* and 8*b* show yet another embodiment of the prosthetic glenoidal component in accordance with the present disclosure in different views.

In FIG. 8a, both a bone interface surface $i_1$ of implant $a_1$ and resected bone surface $i_2$ of bone b receiving bone interface surface $i_1$ are essentially flat.

This geometry leads to tensile forces especially in the areas denoted by a circle.

Figure 8B:
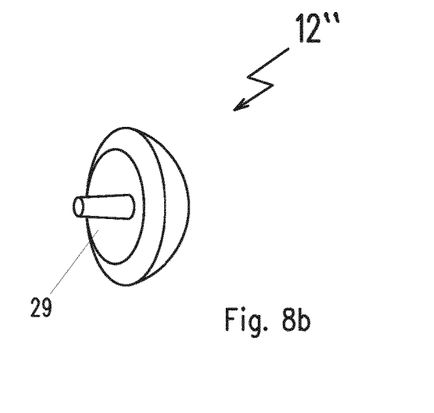

In FIG. 8b, implant $a_2$ is provided with a convex bone interface surface $i_1$ cooperating with a concave resected bone surface $i_2$. Load L generates compressional reaction forces on the upper end of implant $a_1$. In the lower part parasitic tensile forces are generated, again indicated exemplarily by a circle.

In FIG. 8c implant $a_3$ has a concave bone interface surface $i_1$ cooperating with a convex resected bone surface $i_2$. Load L is realigned by this geometry towards a central region of implant $a_3$ thereby greatly reducing the occurrence of tensile forces that are especially detrimental for the fixation of an implant to a bone.

FIGS. 8a and 8b show a further embodiment 12" of a glenoidal component with a concave bone interface surface 29. It can be seen that glenoidal component 12" is more massive than glenoidal components 12, 12' and that the curvature of its articulation surface 16 is larger.

Figures 9, 10:
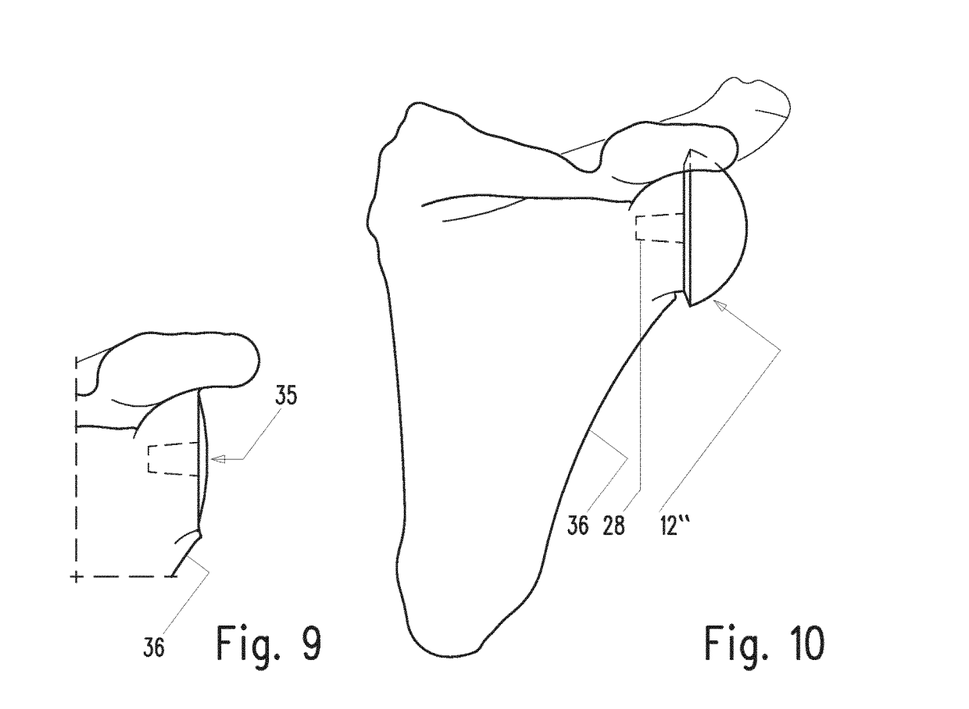
FIG. 9 shows a scapula resected to receive the glenoidal component of FIGS. 9*a* and 9*b*.
FIG. 10 shows the glenoidal component of FIGS. 9*a* and 9*b* attached to the resected scapula.

FIG. 9 shows a portion of a patient's scapula 36 prepared to receive glenoidal component 12". A suitably resected bone surface 35 is convex. The preparation involves only a minor bone resection conserving enough natural bone material for later revisions of the shoulder prosthesis, if needed.

FIG. 10 shows glenoidal component 12" fixed to scapula 36. It should be understood that the fixation of glenoidal component 12" may involve more than one fixation pegs or other suitable fixation means instead of or in addition to peg 28. Bone cement can be used to assist the fixation of glenoidal component 12" to scapula 36.

Figure 11A:
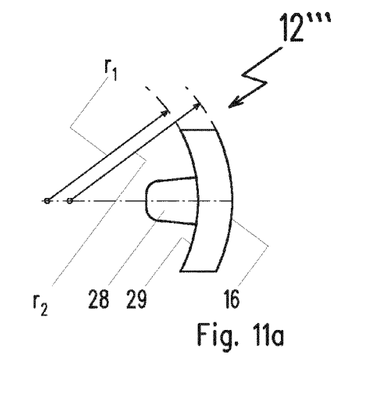
FIGS. 11*a* and 11*b* show a further embodiment of the prosthetic glenoidal component in accordance with the present disclosure.

FIG. 11a shows a further embodiment 12''' of a glenoidal component provided with a relatively massive fixation peg 28—optimized for a press fit—extending from bone interface surface 29. It can be seen that a curvature radius $r_1$ of bone interface surface 29 is smaller than a curvature radius $r_2$ of glenoidal articulation surface 16. The center of radius $r_2$ is shifted towards component 12''' to compensate the fact that surfaces 29, 16 are spaced apart.

Figure 11B:
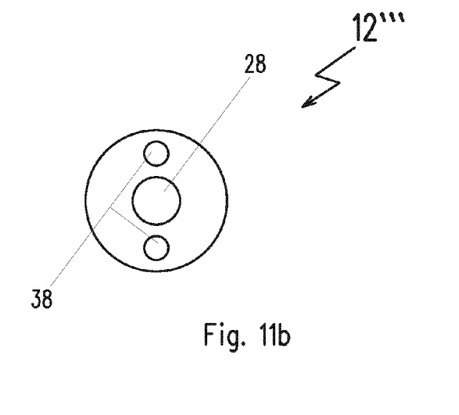

FIG. 11b depicts a backview of glenoidal component 12''' revealing that it is provided—in addition to centrally arranged peg 28—with screw holes 38 that can be used to improve the fixation of glenoidal component 12''' to the bone, if needed. Of course, only one screw hole 38 or more that two screw holes 38 can be provided.

Figure 12:
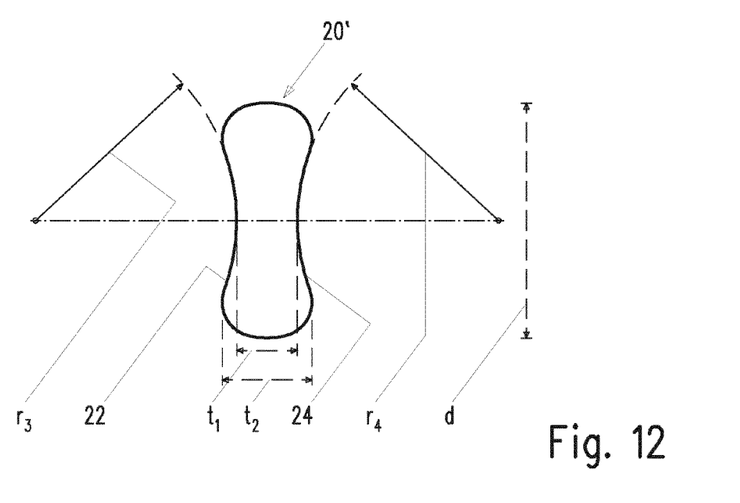
FIGS. 12 to 14 show different embodiments of a glenohumeral bearing component in accordance with the present disclosure.

FIG. 12 shows an lens-like embodiment 20' of a glenohumeral bearing component according to the present disclosure. Both the glenoidal bearing surface 22 and the humeral bearing surface 24 are defined by a specific curvature suitably chosen in consideration of the curvature of the corresponding articulation surface 16, 18, respectively. Specifically, glenoidal bearing surface 22 has a curvature radius $r_3$ and humeral bearing surface 24 has a curvature radius $r_4$. Curvature radii $r_3$, $r_4$ can be chosen as needed, e.g. $r_3 = r_4$, $r_3 > r_4$, $r_3 < r_4$. Further parameters that might be chosen freely in order to obtain the desired kinematics are—inter alia—a diameter d of glenohumeral bearing component 20' or its minimum thickness $t_1$ and/or its maximum thickness $t_2$.

Figure 13:
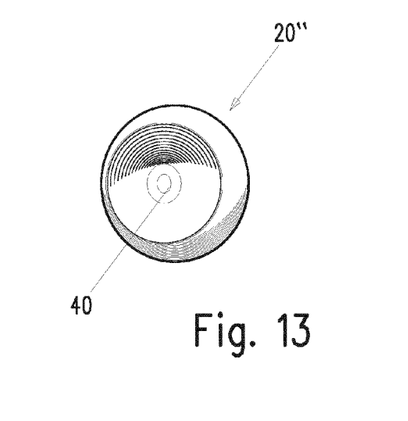
Figure 14:
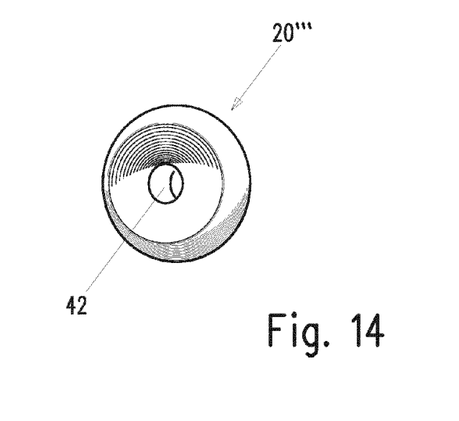

FIGS. 13 and 14 show further embodiments 20", 20''', respectively, of a glenohumeral bearing component according to the present disclosure. Glenohumeral bearing component 20" shown in FIG. 13 is provided with a recess 40 in the center of surfaces 22, 24, so that the contact with articulation surfaces 16, 18, respectively, concentrates in a ring-like region around recess 40.

As it can be seen in FIG. 14, instead of recesses 40, a hole 42 can be provided in a central region of glenohumeral bearing component 20''' in order to save even more material and to reduce its weight. Figuratively speaking, glenohumeral bearing component 20''' is toroidally shaped, i.e. resembles a doughnut. The removal of material in a central region of glenohumeral bearing components 20", 20''' does not compromise the kinematics of the shoulder prosthesis when combined with suitable glenoidal and humeral components.

Figure 15:
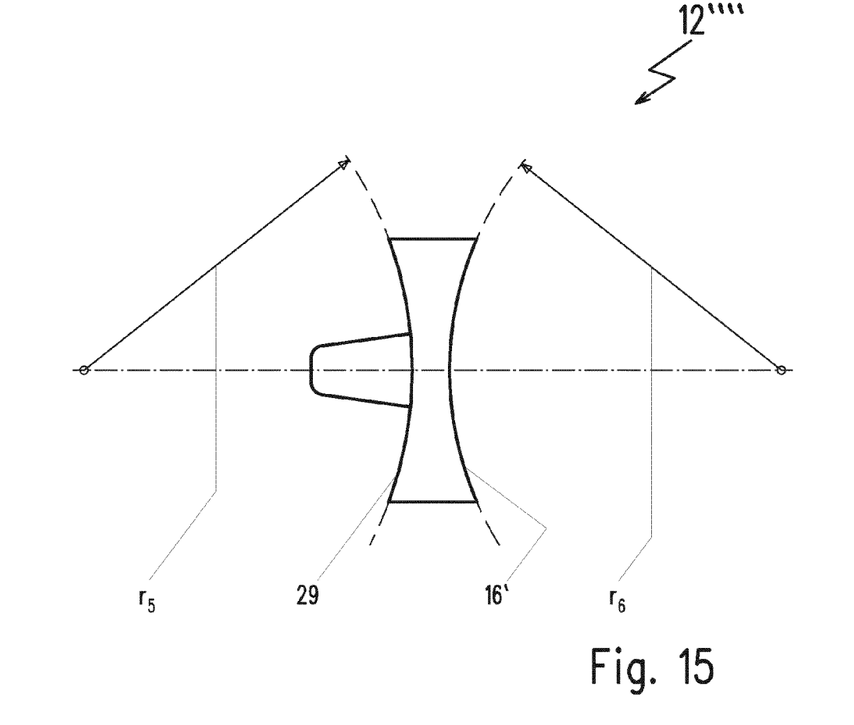
FIG. 15 shows an embodiment of a prosthetic glenoidal component in accordance with the present disclosure and FIG. 16 shows yet another embodiment of a glenohumeral bearing component in accordance with the present disclosure.

FIG. 15 discloses a further embodiment 12'''' of a glenoidal component according to the present disclosure. Glenoidal component 12'''' has a concave bone interface surface 29 with a curvature radius $r_5$ and a concave glenoidal articulation surface 16' with a curvature radius $r_6$. Radii $r_5$, $r_6$ may be equal or different.

Figure 16:
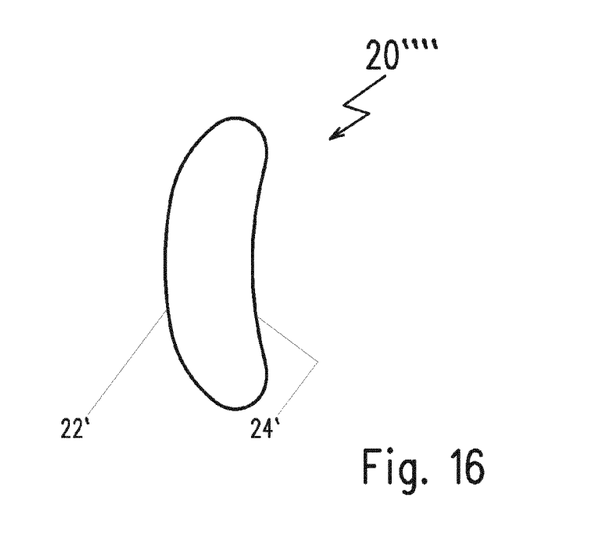

Exemplarily, a glenoidal component 12'''' as depicted in FIG. 15 may be used in combination with a humeral component 14 as shown e.g. in FIGS. 1 to 3. A suitable glenohumeral bearing component 20'''' is shown in FIG. 16. It has a convex glenoidal bearing surface 22' and a concave humeral bearing surface 24'. Hence, glenohumeral bearing component 20'' has a more bean-like appearance compared to the lens-like shape of glenohumeral bearing components 20, 20', 20'', 20'''.

It should be understood that glenohumeral bearing component 20'''' can also be used in shoulder prostheses with a convex glenoidal articulation surface and a concave humeral articulation surface.

LIST OF REFERENCE NUMBERS 10, 10' shoulder prosthesis
12, 12', 12'', 12''', 12'''' glenoidal component
14 humeral component
16, 16' glenoidal articulation surface
18 humeral articulation surface
20, 20', 20'', 20''', 20'''' glenohumeral bearing component
22, 22' glenoidal bearing surface
24, 24' humeral bearing surface
26 humerus
28 peg
29, 29' bone interface surface
30 base element
32 articulation element
34a, 34b contacting surface
35 resected bone surface
36 scapula
38 screw hole
40 recess
42 hole
$r_1$, $r_2$, $r_3$, $r_4$, $r_5$, $r_6$ curvature radius
$a_1$, $a_2$, $a_3$ implant
L, l load
b bone
$i_1$ bone interface surface
$i_2$ resected bone surface
$t_1$, $t_2$ thickness
d diameter

The invention claimed is:

1. A shoulder prosthesis comprising:
    a glenoidal component having a glenoidal articulation surface;
    a humeral component having a humeral articulation surface; and
    a separate mobile glenohumeral bearing component comprising an exterior glenoidal bearing surface and an exterior humeral bearing surface arranged on opposite sides of the glenohumeral bearing component, wherein the glenohumeral bearing component is disposed, in an implanted state, between the glenoidal component and the humeral component such that at least one of the glenoidal bearing surface and the humeral bearing surface contacts the corresponding glenoidal articulation surface or humeral articulation surface;
    wherein at least one of the glenoidal and humeral bearing surfaces is concave;
    wherein both the glenoidal and humeral articulation surfaces are convex; and
    wherein when the glenohumeral bearing component is in an implanted state, the glenohumeral bearing component is mobile relative to at least one of the glenoidal component and the humeral component.

2. The shoulder prosthesis according to claim 1, wherein the glenoidal and humeral bearing surfaces have different curvatures or comprise different sizes.

3. The shoulder prosthesis according to claim 1, wherein the glenohumeral bearing component comprises at least one of a central recess in the glenoidal bearing surface and a central opening extending from the glenoidal bearing surface to the humeral bearing surface.

4. The shoulder prosthesis according to claim 1, wherein the glenoidal component comprises a glenoidal bone interface provided to be attached to a scapula of a patient and/or wherein the humeral component comprises a humeral bone interface provided to be attached to a humerus of a patient, wherein the glenoidal interface or the humeral bone interface is concave.

5. The shoulder prosthesis according to claim 4, wherein the glenoidal bone interface is disposed on a glenoidal base element that couples with an articulation element of the glenoidal component carrying the glenoidal articulation surface via a first coupling means and/or wherein the humeral bone interface is disposed on a humeral base element that couples with an articulation element of the prosthetic humeral component carrying the humeral articulation surface via a second coupling means.

6. The shoulder prosthesis according to claim 1, wherein the glenohumeral bearing component is made of ceramic, polyethylene, or a combination thereof.

7. The shoulder prosthesis according to claim 1, wherein the glenoidal articulation surface, the humeral articulation surface, the glenoidal bearing surface and the humeral bearing surface are designed such that a first coefficient of friction between the glenoidal articulation surface and the glenoidal bearing surface and a second coefficient of friction between the humeral articulation surface and the humeral bearing surface are essentially equivalent.

8. The shoulder prosthesis according to claim 1, wherein one of the glenoidal bearing and the humeral bearing surfaces is concave and the other of the glenoidal bearing and the humeral bearing surfaces is one of planar, convex or concave.

9. A method for implanting a shoulder prosthesis comprising the steps of:
    providing or obtaining a prosthetic glenoidal component comprising a glenoidal articulation surface, wherein the glenoidal articulation surface is convex;
    resecting a glenoidal portion of a patient's scapula and attaching the glenoidal component to the resected glenoidal portion;
    providing or obtaining a prosthetic humeral component comprising a humeral articulation surface, wherein the humeral articulation surface is convex;
    resecting a proximal end portion of a patient's humerus and attaching the humeral component to the resected proximal end portion; and
    inserting a mobile glenohumeral bearing component comprising an exterior glenoidal bearing surface and an exterior humeral bearing surface, wherein at least one of the glenoidal bearing surface and the humeral bearing surface contacts, in an implanted state, the corresponding glenoidal articulation surface or humeral articulation surface;

wherein when the glenohumeral bearing component is in the implanted state, the glenohumeral bearing component is mobile relative to at least one of the glenoidal component and the humeral component.

10. The method according to claim 9, wherein the step of resecting the glenoidal portion of a patient's scapula comprises preparing a convex bone portion adapted to match a correspondingly shaped bone interface of the glenoidal component.

11. The method according to claim 10, wherein the step of attaching the glenoidal component to the resected glenoidal portion comprises placing the glenoidal component on the convex bone portion and fixing it to the scapula using at least one of a screw, bone cement and a press-fit means.

12. The method according to claim 11, wherein the glenoidal bone interface is concave.

13. The method according to claim 9, wherein at least one of the glenoidal and humeral bearing surfaces is concave.

14. A shoulder prosthesis comprising:
a glenoidal component having a glenoidal articulation surface;
a humeral component having a humeral articulation surface; and
a separate mobile glenohumeral bearing component comprising a glenoidal bearing surface and a humeral bearing surface arranged on opposite sides of the glenohumeral bearing component, wherein the glenohumeral bearing component is disposed, in an implanted state, between the glenoidal component and the humeral component such that the glenoidal and humeral bearing surfaces contact the corresponding glenoidal and humeral articulation surfaces, without securing, fixing, or otherwise attaching the glenohumeral bearing component to the glenoidal component and the humeral component;

wherein at least one of the glenoidal and humeral bearing surfaces is concave;

wherein both the glenoidal and humeral articulation surfaces are convex; and wherein when the glenohumeral bearing component is in an implanted state, the glenohumeral bearing component is mobile relative to the glenoidal component and the humeral component, due to the absence of physical attachment between the glenohumeral bearing component and the glenoidal and humeral components, thereby enabling the glenohumeral bearing component to move freely and articulate relative to the glenoidal articulation surface and the humeral articulation surface.

15. The shoulder prosthesis according to claim 1, wherein the glenohumeral bearing component is peanut shaped.

16. The shoulder prosthesis according to claim 1, wherein the glenohumeral bearing component is lens shaped.

* * * * *